United States Patent
Lecomte et al.

(10) Patent No.: US 9,017,421 B2
(45) Date of Patent: Apr. 28, 2015

(54) PROSTHETIC FOOT WITH DUAL FOOT BLADES AND VERTICALLY OFFSET TOE

(75) Inventors: Christophe Lecomte, Reykjavik (IS); Vilhjalmur Freyr Jónsson, Reykjavik (IS); Maria Gudrun Sveinbjornsdottir, Mosfellsbær (IS); Benedikt Skulason, Reykjavik (IS)

(73) Assignee: Össur hf, Reykjavik (IS)

(*) Notice: Subject to any disclaimer, the term of this patent is extended or adjusted under 35 U.S.C. 154(b) by 0 days.

(21) Appl. No.: 13/309,418

(22) Filed: Dec. 1, 2011
(Under 37 CFR 1.47)

(65) Prior Publication Data
US 2013/0144403 A1    Jun. 6, 2013

(51) Int. Cl.
*A61F 2/68* (2006.01)
*A61F 2/66* (2006.01)

(52) U.S. Cl.
CPC .......... *A61F 2/66* (2013.01); *A61F 2002/6621* (2013.01)

(58) Field of Classification Search
USPC ........................................................... 623/53
See application file for complete search history.

(56) References Cited

U.S. PATENT DOCUMENTS

| | | |
|---|---|---|
| 2,440,075 A | 4/1948 | Campbell |
| 4,892,553 A | 1/1990 | Prahl |
| 5,037,444 A | 8/1991 | Phillips |
| 5,062,859 A | 11/1991 | Naeder |
| 5,514,185 A | 5/1996 | Phillips |
| 5,514,186 A | 5/1996 | Phillips |
| 5,545,230 A | 8/1996 | Kinsinger et al. |
| 5,800,570 A | 9/1998 | Collier |
| 5,976,191 A | 11/1999 | Phillips |
| 6,071,313 A | 6/2000 | Phillips |
| 6,077,301 A | 6/2000 | Pusch |
| 6,099,572 A | 8/2000 | Mosler et al. |
| 6,165,227 A | 12/2000 | Phillips |
| 6,241,776 B1 | 6/2001 | Christensen |

(Continued)

FOREIGN PATENT DOCUMENTS

| | | |
|---|---|---|
| SU | 1454449 | 1/1989 |
| SU | 1600759 | 10/1990 |
| WO | WO 2011/066354 | 6/2011 |

OTHER PUBLICATIONS

BioQuest Perfect Stride brochure, http://bioquestpros.com/BioQuest_Prosthetics/Products_files/PS2_X3.pdf, believed to have been released in 2006.

(Continued)

*Primary Examiner* — Jacqueline Woznicki
(74) *Attorney, Agent, or Firm* — Knobbe, Martens, Olson & Bear, LLP.

(57) ABSTRACT

Prosthetic feet having improved vertical suspension are provided. A prosthetic foot can include a foot member having a change in curvature near a toe section so that the toe section is downwardly vertically offset from the remainder of the foot member. A prosthetic foot can have upper and lower foot members that extend parallel to each other and are separated by a gap. The lower foot member can extend beyond a distal end of the upper foot member to form a toe section. An adapter for coupling a prosthetic foot to another prosthetic component is also provided. The adapter includes a cavity for receiving the proximal end of a prosthetic foot. The prosthetic foot is secured to the adapter with a curable material such as epoxy to provide a more lightweight system.

21 Claims, 9 Drawing Sheets

(56) References Cited

U.S. PATENT DOCUMENTS

| | | |
|---|---|---|
| 6,406,500 B1 | 6/2002 | Phillips |
| 6,514,293 B1 | 2/2003 | Jang et al. |
| 6,527,811 B1 | 3/2003 | Phillips |
| 6,706,075 B1 | 3/2004 | Laghi |
| 6,719,807 B2 | 4/2004 | Harris |
| 6,793,683 B1 | 9/2004 | Laghi |
| 6,875,240 B1 | 4/2005 | Laghi |
| 7,112,227 B2 | 9/2006 | Doddroe et al. |
| 7,172,630 B2 | 2/2007 | Christensen |
| 7,211,115 B2 | 5/2007 | Townsend et al. |
| 7,374,578 B2 | 5/2008 | Townsend et al. |
| 7,410,503 B2 | 8/2008 | Townsend et al. |
| 7,429,272 B2 | 9/2008 | Townsend et al. |
| 7,507,259 B2 | 3/2009 | Townsend et al. |
| 7,578,852 B2 | 8/2009 | Townsend et al. |
| 7,611,543 B2 | 11/2009 | Townsend et al. |
| 7,648,533 B2 | 1/2010 | Phillips et al. |
| 7,686,848 B2 | 3/2010 | Christensen |
| 7,708,784 B2 | 5/2010 | Townsend et al. |
| 7,727,285 B2 | 6/2010 | Christensen et al. |
| 7,824,446 B2 | 11/2010 | Christensen et al. |
| 7,846,213 B2 | 12/2010 | Lecomte et al. |
| 7,879,110 B2 | 2/2011 | Phillips |
| 7,955,399 B2 | 6/2011 | Townsend et al. |
| 7,998,221 B2 | 8/2011 | Lecomte et al. |
| 8,007,544 B2 | 8/2011 | Jonsson et al. |
| 8,034,121 B2 | 10/2011 | Christensen |
| 8,771,372 B1 | 7/2014 | Rubie et al. |
| 2002/0077706 A1 | 6/2002 | Phillips |
| 2003/0144745 A1 | 7/2003 | Phillips |
| 2006/0030950 A1 | 2/2006 | Townsend et al. |
| 2006/0212131 A1 | 9/2006 | Curtis |
| 2007/0106395 A9* | 5/2007 | Clausen et al. ............... 623/52 |
| 2007/0213840 A1 | 9/2007 | Townsend et al. |
| 2008/0188950 A1 | 8/2008 | Fleury et al. |
| 2008/0228288 A1 | 9/2008 | Nelson et al. |
| 2008/0281436 A1 | 11/2008 | Townsend et al. |
| 2008/0312752 A1 | 12/2008 | Miller |
| 2009/0157197 A1 | 6/2009 | Bonacini |
| 2009/0204231 A1 | 8/2009 | Bonacini |
| 2010/0023135 A1 | 1/2010 | Rubie et al. |
| 2010/0042228 A1 | 2/2010 | Doddroe et al. |
| 2010/0312360 A1 | 12/2010 | Caspers |
| 2011/0093089 A1 | 4/2011 | Martin |
| 2011/0213471 A1 | 9/2011 | Jonsson |
| 2011/0230976 A1 | 9/2011 | Zarling et al. |

OTHER PUBLICATIONS

BioQuest Bio Stride brochure, http://bioquestpros.com/BioQuest_Prosthetics/Products_files/BioStride_Series.pdf, believed to have been released in 2010.

College Park Velocity™ brochure, http://www.college-park.com/images/pdf/cpi-product-velocity.pdf, believed to have been released in 2011.

Fillauer Wave Comfort Foot System™ Information Sheet, http://www.fillauer.com/pdf/AD315-Wave-Comfort-Foot-System.pdf, Sep. 1, 2011.

Freedom Innovations Thrive™ brochure, http://www.freedom-innovations.com/thrive/, Sep. 2010.

Freedom Innovations WalkTek™ brochure, http://www.freedom-innovations.com/walktek/, May 2011.

Ohio Willow Wood Trailblazer™ product, http://www.willowwoodco.com/products-and-services/feet/high-activity/trailblazer, believed to have been released in 2006.

Otto Bock Triton products, http://www.ottobock.com/cps/rde/xchg/ob_com_en/hs.xsl/38134.html, believed to have been released Jun. 2011.

Feb. 7, 2013 International Search Report and Written Opinion for International Application No. PCT/US2012/066888 filed on Nov. 28, 2012.

Otto Bock C-Sprint® product, Otto Bock Prosthetics—Lower Extremities Catalog, p. 102, 2008.

Flex-Foot Flex-Walk Double C product catalog page; 1997.

Flex-Foot Vari-Flex product including dual foot blades, 1997.

* cited by examiner

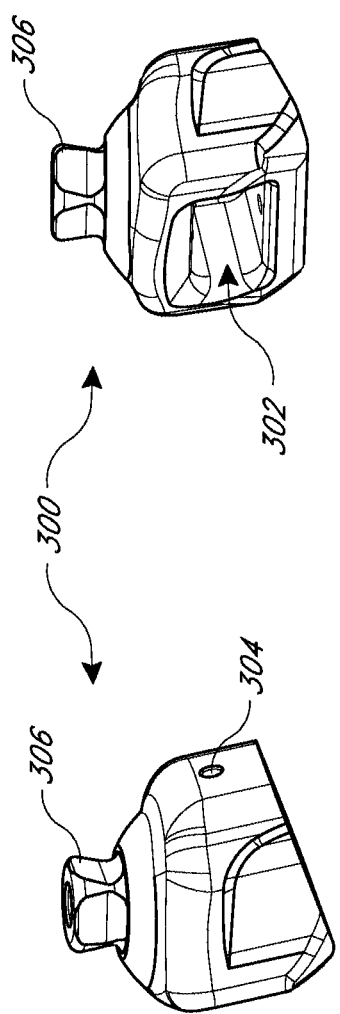

PROSTHETIC FOOT WITH DUAL FOOT BLADES AND VERTICALLY OFFSET TOE

BACKGROUND

1. Field

The present application relates to foot prostheses in general, and more particularly, to prosthetic feet having dual foot blades and/or an offset toe portion.

2. Description of the Related Art

Various types of prosthetic foot devices are available as substitutes for human feet. Some common problems are often observed in conventional mechanical prosthetic feet, for example limited vertical suspension during ambulation. Some conventional designs incorporate shocks to provide enhanced vertical suspension; however, such designs are often bulky and heavy, which may require the user to exert more force to walk.

Accordingly, there is a need for a lightweight and durable prosthetic foot having enhanced vertical suspension characteristics.

SUMMARY

In some embodiments, a prosthetic foot includes an elongate foot member extending from a proximal portion to a distal portion. The proximal and distal portions are generally horizontal, and the foot member has a curved portion between the proximal and distal portions. The proximal portion is generally at a location of a natural human ankle and is configured to be coupled to an adapter. The distal portion includes a change in curvature that defines a toe region of the foot member. The toe region is downwardly vertically offset from a portion of the foot member proximal of the change in curvature.

In some embodiments, a prosthetic foot includes an elongate, generally concave upper foot member and an elongate, generally concave lower foot member. The upper foot member extends from a proximal end configured to be coupled to an adapter to a distal end. The lower foot member extends from a proximal end configured to be coupled to the adapter to a distal end. The lower foot member is substantially parallel to the upper foot member and extends distally beyond the distal end of the upper foot member to form a toe region. The upper and lower foot members are coupled at their proximal ends and via one or more fasteners near the distal end of the upper foot member. The lower foot member includes a change in curvature distal to the one or more fasteners so that the toe region is downwardly vertically offset from a portion of the lower foot member proximal of the change in curvature. The upper and lower foot members are separated by a gap when the prosthetic foot is at rest. The gap extends between the coupled proximal ends of the upper and lower foot members and the one or more fasteners.

In some embodiments, an adapter for a prosthetic foot includes a cavity configured to receive a proximal end of a prosthetic foot. The adapter also includes one or more apertures in a surface of the adapter that are in fluid communication with the cavity.

For purposes of summarizing the disclosure and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the disclosure may be embodied or carried out in a manner that achieves or optimizes one advantage or group of advantages as taught or suggested herein without necessarily achieving other objects or advantages as may be taught or suggested herein.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIG. 3A is a front perspective view of one embodiment of an adapter for a prosthetic foot;

FIG. 3B is a rear perspective view of the adapter of FIG. 3A;

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Figure 1A:
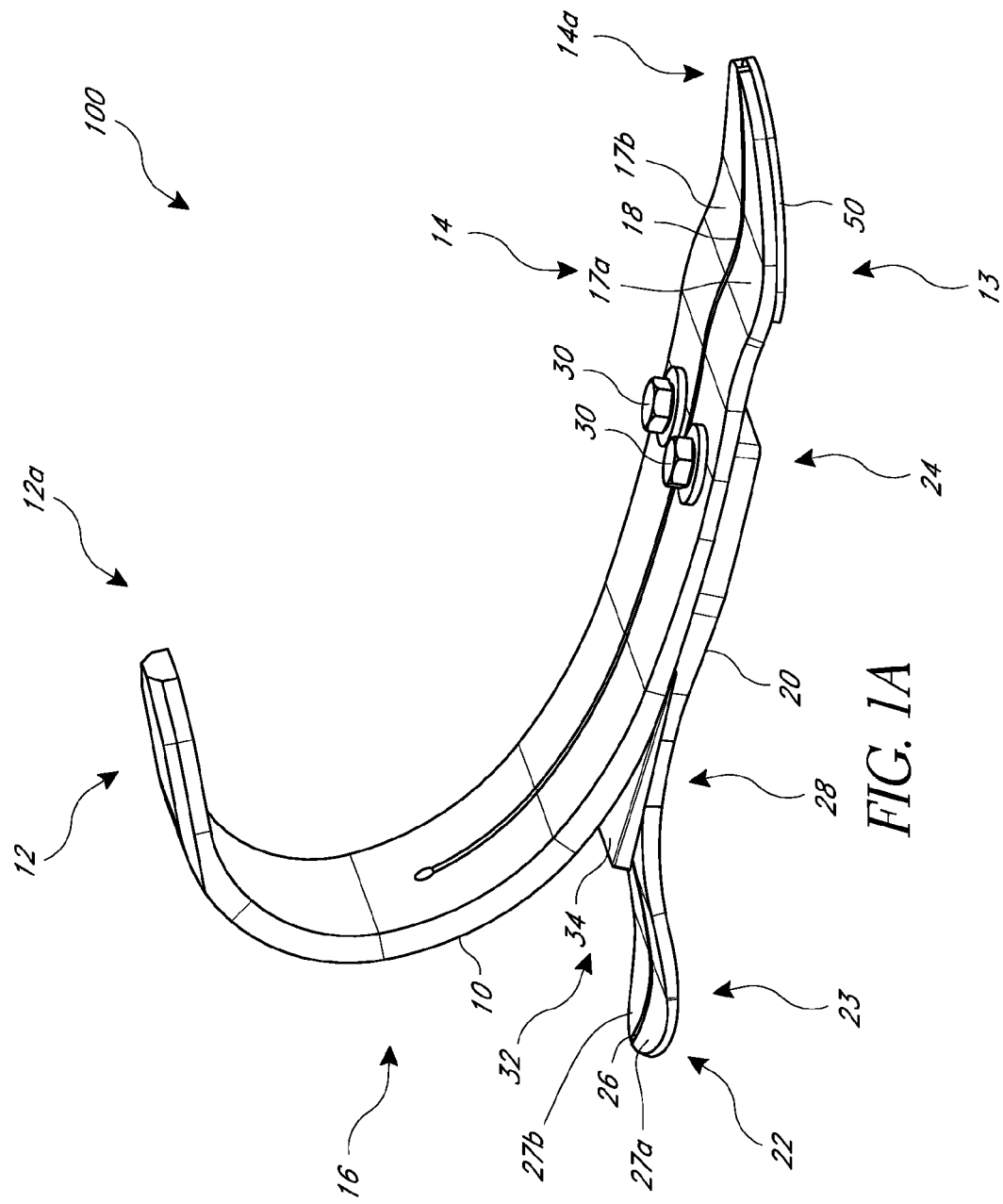
FIG. 1A shows a front perspective view of one embodiment of a prosthetic foot.
Figure 1B:
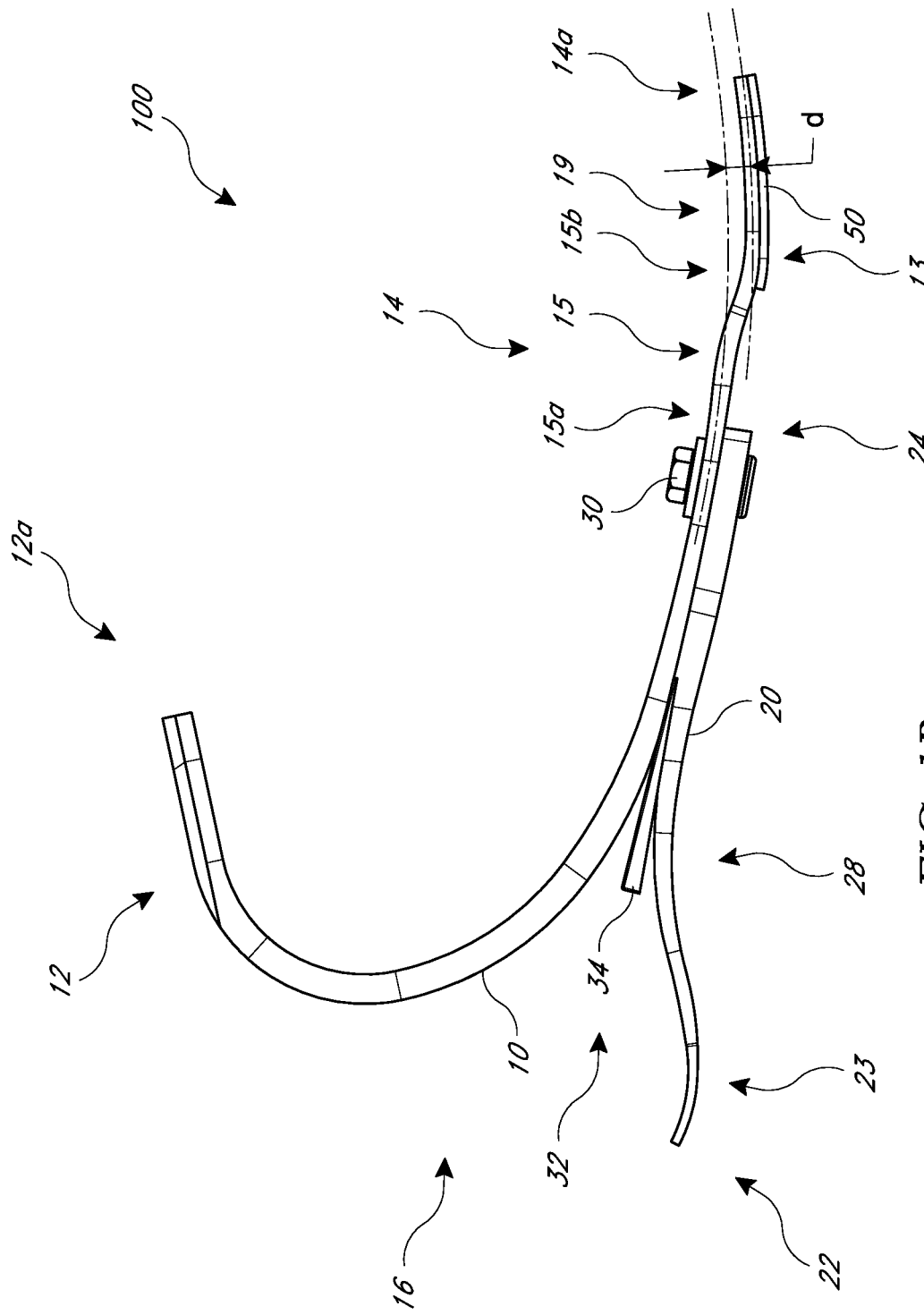
FIG. 1B is a side view of the prosthetic foot illustrated in FIG. 1A.

FIGS. 1A-1B illustrate an example embodiment of a prosthetic foot 100. The prosthetic foot 100 has a foot member 10 that extends from a proximal section 12 to a distal section 14. The proximal section 12 can extend to a proximal end 12a. The distal section 14 can extend to a distal end 14a generally at a location of natural human toes. In the illustrated embodiment, the proximal section 12 can be generally horizontally oriented, and the distal section 14 can be generally horizontally oriented. The prosthetic foot 10 can have a curved portion 16 between the proximal section 12 and distal section 14. Curved portion 16 is generally forwardly-facing concave so that the foot member 10 in the illustrated embodiment is generally C-shaped. In some embodiments, curved portion 16 and/or proximal section 12 can be generally at a location of a natural human ankle. Curved portion 16 can also have a predetermined length that provides the foot 100 with a desired flexibility. For example, in some embodiments, the curved portion 16 can be made more flexible by making it longer while still keeping it within a range of natural human anatomy. In other embodiments, the proximal section 12 can be generally vertically oriented, and the distal section 14 can be generally horizontally oriented, with the foot member 10 curving downward and forward from the proximal section 12 to the distal section 14 (e.g., having a J-shape). In other embodiments, the distal section 14 is generally horizontally oriented and the proximal section 12 is inclined at an angle relative to the distal section 14 and relative to a support surface so that foot member 10 is inclined from the proximal end 12a downward and forward to the distal end 14a.

The prosthetic foot 100 can also have a heel member 20 that extends rearwardly from a distal end 24 to a free proximal end 22 and is disposed below at least a portion of the foot member 10. In some embodiments, the heel member 20 can be coupled to the foot member 10 via one or more fasteners 30 (e.g., bolts) proximate the distal end 24 of the heel member 20 at a location between the proximal 12a and distal 14a ends of the foot member 10 such that the heel member 20 is cantilevered relative the foot member 10. The heel member 20 can have a curvilinear profile along its length that defines an arch 28 between the proximal end 22 and distal end 24.

In some embodiments, the distal section 14 of the foot member 10 includes a change in curvature so that the distal section 14 has a segment 15 of downward curvature and a toe section 19 that is downwardly vertically offset from the remainder of the foot member 10 proximal to the toe section 19 as illustrated by distance d in FIG. 1B. In some embodiments, distance d is in the range of about 0 mm to about 15 mm, for example about 0 mm to about 10 mm. In some embodiments, the segment 15 of downward curvature is short so that the change in curvature is a step-like change. In other embodiments, the segment 15 is slightly longer so that the change in curvature is a more gradual change. The change in curvature of the foot member 10 is distal to the one or more fasteners 30 coupling the heel member 20 to the foot member 10. In some embodiments, the segment 15 of downward curvature is in a location corresponding to the metatarsal joint in a natural human foot. The distal section 14 of the foot member 10 can be generally concave on both the proximal 15a and distal 15b sides of the segment 15 of downward curvature. In some embodiments, a radius of curvature of the distal section 14 of the foot member 10 is the same on the proximal 15a and distal 15b sides of the segment 15 of downward curvature so that the only change in the distal section 14 of the foot member 10 is the vertical offset d. In other embodiments, the radius of curvature of the distal section 14 is different on the proximal 15a and distal 15b sides of the segment 15 of downward curvature. For example, the radius of curvature on the proximal side 15a of the segment 15 of downward curvature can be chosen to correspond to the curvature of the distal end 24 of the heel member 20 so that the foot 10 and heel 20 members can be placed adjacent each other and coupled via the fasteners 30. The radius of curvature on the distal side 15b of the segment 15 of downward curvature can be chosen to promote a smooth rollover of the foot member 10 during ambulation.

The drop-down or vertically offset toe section 19 feature advantageously allows for the foot 100 to be supported during stance at portions of the heel 23 and toe 13, rather than at the heel 23 and fasteners 30 as in previous designs. This allows for enhanced suspension and increased vertical displacement of the prosthetic foot 100 during stance because the fasteners 30 are not in contact with the ground. For example, in one embodiment, the displaced toe section 19 allows a vertical displacement of up to approximately 10 mm at mid-stance. In some embodiments, the displaced toe section 19 allows a vertical displacement of approximately 5 to approximately 15 mm at mid-stance. In some embodiments, the displaced toe section 19 allows a vertical displacement of greater than 10 mm at mid-stance. The enhanced suspension advantageously provides a softer (e.g., dampened) mid-stance roll-over. The displaced toe section 19 also provides for improved toe-off during ambulation.

The foot 10 and heel 20 members can define a slot 32 therebetween in the fore-aft direction at a rear portion of the prosthetic foot 100. In some embodiments, the slot 32 can taper toward a front end of the prosthetic foot 100. A resilient member 34 can be disposed between the heel member 20 and the foot member 10 within the slot 32. In some embodiments, the resilient member 34 can separate at least a portion of the foot member 10 from the heel member 20. In some embodiments, the resilient member can completely separate the foot member 10 from the heel member 20.

In some embodiments, the resilient member 34 is removably disposed in the slot 32 between the heel member 20 and foot member 10. Optionally, a plurality of resilient members 34 can be disposed in the slot 32. In other embodiments, the resilient member 34 can be fixed in the slot 32 via, for example, an adhesive. Various other mechanisms can be used to fix the resilient member 34 in the slot 32. For example, the resilient member 34 can be bolted or screwed to the heel member 20 and/or the foot member 10. The resilient member 34 can provide additional shock absorption to the prosthetic foot 100. In some embodiments, the resilient member 34 can be made, for example, of a hard plastic, such as polyurethane or polypropylene. The resilient member 34 can also be made of a more compressible material, such as foam, natural or synthetic rubbers, or the like. However, the resilient member 34 can be made of any material that provides adequate shock absorption to the prosthetic foot 100. A set of such resilient members 34 can also be provided, wherein each resilient member 34 has a different stiffness. Further details on prosthetic feet, including further information on resilient members, among other things, can be found in U.S. Pat. No. 8,007,544, filed Aug. 15, 2003, the entire contents of which are incorporated herein by reference and should be considered a part of this specification.

In some embodiments, a crepe portion 50 can be attached to a bottom surface of a portion of the distal section 14 of the foot member 10 and aligned so as to not extend past the distal end 14a of the foot member 10. In other embodiments, the crepe portion 50 can extend forwardly of the distal end 14a of the foot member 10.

The crepe portion 50 can be a resilient pad or cushion made of a compressible material. In some embodiments, the crepe portion 50 can be made of a porous material or solid urethane. In some embodiments, the crepe portion 50 is attached to the foot member 10 with an adhesive. However, other attachment mechanisms can be used, such as bolts, screws, clamps, and/or bands wrapped around the crepe portion 50 and the foot member 10. The crepe portion 50 can have a shape corresponding to the shape of the foot member 10. For example, the crepe portion 50 can have a rounded edge corresponding to a rounded edge of the distal end 14a of the foot member 10. In the illustrated embodiment, the crepe portion 50 has a uniform thickness. In other embodiments, the crepe portion 50 can have a varying thickness. For example, the crepe portion 50 can have a decreasing thickness in the direction of the distal end 14a of the foot member 10. In other embodiments, the foot member 10 does not have a crepe portion 50 attached to it so that a portion of the distal section 14 the foot member 10 operatively contacts the support surface. Further details on prosthetic feet, including further details on foot members and crepe portions, can be found in U.S. Pat. No. 8,007,544, which is incorporated by reference in its entirety herein.

As shown in FIG. 1A, the foot member 10 can have multiple elongate segments that can flex independently relative to each other. In the illustrated embodiment, the foot member 10 has two elongate segments 17a, 17b that are separated from each other by a split (or slot) 18 that extends along a length between the distal end 14a and the proximal end 12a of the foot member 10. In some embodiments, the split 18 extends along the entire length of the foot member 10. In some embodiments, the split 18 extends along a length that is shorter than the entire length of the foot member 10. In the illustrated embodiment, the split extends from an opening in the curved portion 16 of the foot member 10 to the distal end 14a of the foot member 10. In some embodiments, the split 18 extends linearly along its length, so that the width of the elongate segments 17a, 17b in a direction transverse to the length of the foot is generally the same along their lengths. In some embodiments, the split 18 can have a curved section, such that one of the elongate segments 17a, 17b has a different transverse width than another of the elongate segments 17a, 17b over at least a portion of their lengths.

The heel member 20 can also have multiple elongate segments that can flex independently relative to each other. In the illustrated embodiment, the heel member 20 has two elongate segments 27a, 27b that are separated from each other by a split (or slot) 26 that extends along a length between the distal end 24 and the proximal end 22 of the heel member 20. In some embodiments, for example as shown in FIG. 1, the split 26 extends along the entire length of the heel member 20. In some embodiments, the split 26 extends along a length that is shorter than the entire length of the heel member 20. In some embodiments, the split 26 extends linearly along its length, so that the transverse width of the elongate segments 27a, 27b is generally the same along their lengths. In some embodiments, the split 26 can have a curved section, such that one of the elongate segments 27a, 27b has a different transverse width than another of the elongate segments 27a, 27b over at least a portion of their lengths. In some embodiments, the split 26 in the heel member 20 aligns with the split 18 in the foot member 10.

In some embodiments, the foot 10 and heel 20 members are plate-like members with generally planar top and bottom surfaces and generally rectangular transverse cross-sections. The foot 10 and heel 20 members can be made of lightweight resilient materials, such as one or more of graphite, fiberglass, carbon fiber, and the like. In some embodiments, the foot 10 and heel 20 members can be formed of multiple layers of material that define a monolithic piece.

Figure 2A:
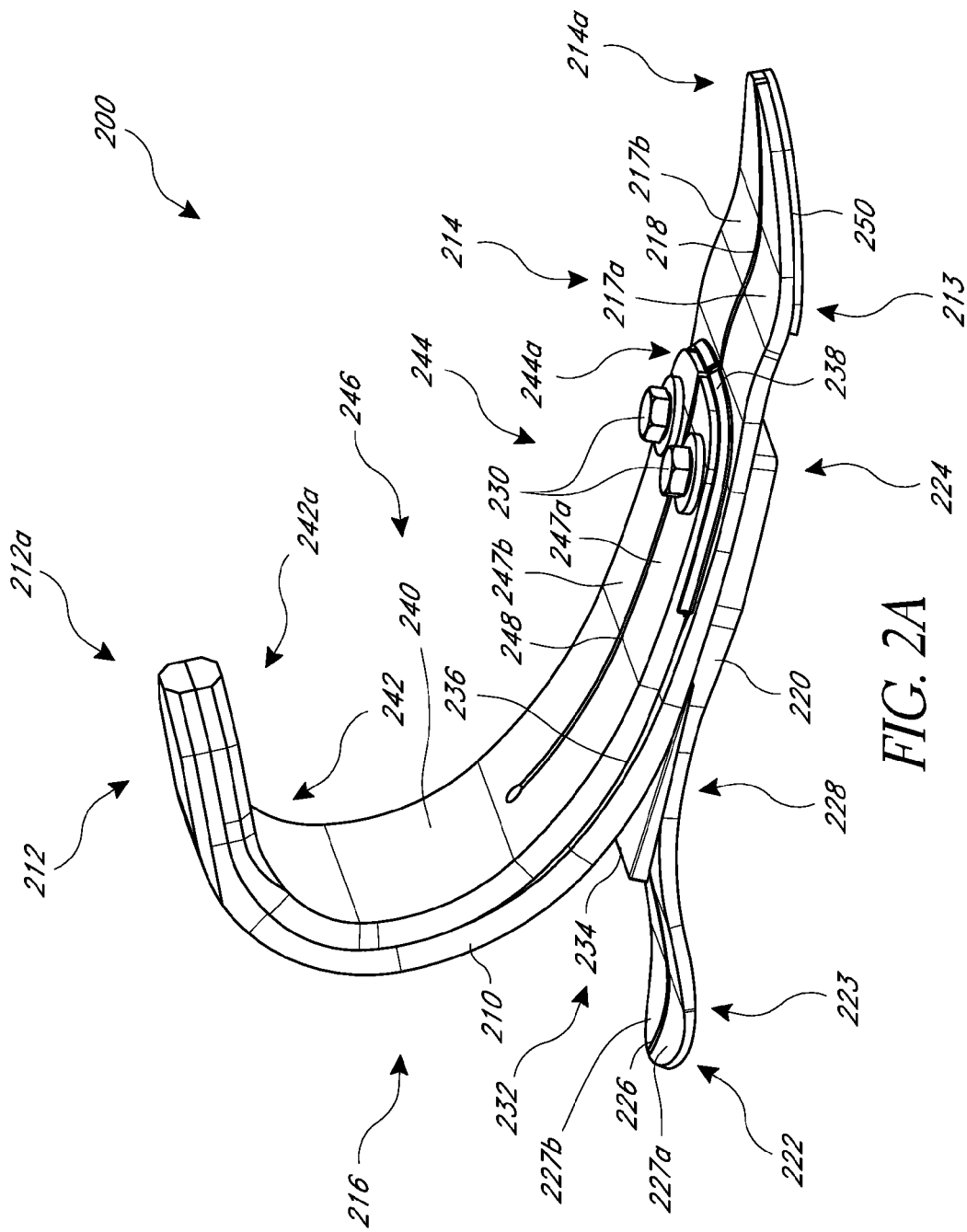
FIG. 2A is a front perspective view of another embodiment of a prosthetic foot.
Figure 2B:
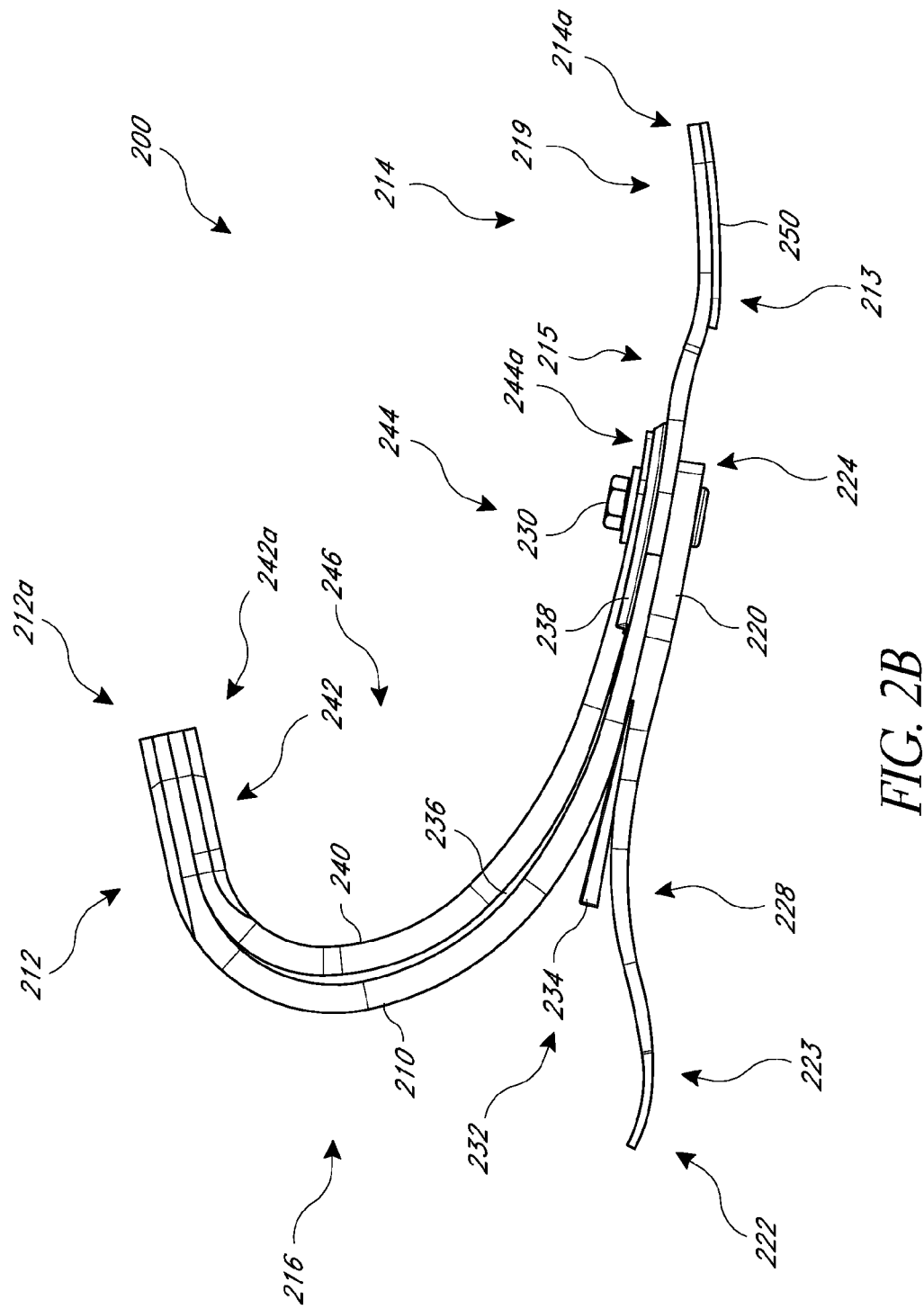
FIG. 2B is a side view of the prosthetic foot of FIG. 2A.

FIGS. 2A-2B illustrate an example embodiment of a prosthetic foot 200 having dual foot blades. The prosthetic foot 200 has an upper foot member 240 that extends from a proximal section 242 to a distal section 244. The proximal section 242 can extend to a proximal end 242a. The distal section 244 can extend to a distal end 244a. In the illustrated embodiment, the proximal section 242 can be generally horizontally oriented, and the distal section 244 can be generally horizontally oriented. Upper foot member 240 can have a curved portion 246 between the proximal section 242 and distal section 244. Curved portion 246 is generally forwardly-facing concave so that the upper foot member 240 in the illustrated embodiment is generally C-shaped. In some embodiments, curved portion 246 and/or proximal section 242 can be generally at a location of a natural human ankle. In other embodiments, the proximal section 242 can be generally vertically oriented, and the distal section 244 can be generally horizontally oriented, with the upper foot member 240 curving downward and forward from the proximal section 242 to the distal section 244 (e.g., having a J-shape). In other embodiments, the distal section 244 is generally horizontally oriented and the proximal section 242 is inclined at an angle relative to the distal section 244 and relative to a support surface so that foot member 240 is inclined from the proximal end 242a downward and forward to the distal end 244a.

The prosthetic foot 200 also has a lower foot member 210, which is disposed generally below the upper foot member 240. Lower foot member 210 can be similar to the foot member 10 of prosthetic foot 100 shown in FIGS. 1A-1B and described herein. Lower foot member 210 extends from a proximal section 212 to a distal section 214. The proximal section 212 can extend to a proximal end 212a. The distal section 214 can extend to a distal end 214a generally at a location of natural human toes. In the illustrated embodiment, the proximal section 212 can be generally horizontally oriented, and the distal section 214 can be generally horizontally oriented. Lower foot member can have a curved portion 216 between the proximal section 212 and distal section 214. Curved portion 216 is generally forwardly-facing concave so that the lower foot member 210 in the illustrated embodiment is generally C-shaped. In some embodiments, curved portion 216 and/or proximal section 212 can be generally at a location of a natural human ankle. In other embodiments, the proximal section 212 can be generally vertically oriented, and the distal section 214 can be generally horizontally oriented, with the foot member 210 curving downward and forward from the proximal section 212 to the distal section 214 (e.g., having a J-shape). In other embodiments, the distal section 214 is generally horizontally oriented and the proximal section 212 is inclined at an angle relative to the distal section 214 and relative to a support surface so that foot member 210 is inclined from the proximal end 212a downward and forward to the distal end 214a.

The prosthetic foot 200 can have a heel member 220 that extends rearwardly from a distal end 224 to a free proximal end 222 and is disposed below at least a portion of the lower foot member 210. In some embodiments, the heel member 220 can be coupled to the lower foot member 210 via one or more fasteners 230 (e.g., bolts) proximate the distal end 224 of the heel member 220 at a location between the proximal 212a and distal 214a ends of the lower foot member 210 such that the heel member 220 is cantilevered relative the lower foot member 210. The heel member 220 can have a curvilinear profile along its length that defines an arch 228 between the proximal end 222 and distal end 224.

In the illustrated embodiment, the upper 240 and lower 210 foot members extend generally parallel to each other and have generally the same shape (e.g., a C-shape). Curved portions 246, 216 of upper 240 and lower 210 foot members can have predetermined lengths to provide the foot 200 with a desired flexibility. For example, in some embodiments, the curved portions 246, 216 can be made more flexible by making them longer while still keeping them within a range of natural human anatomy. In some embodiments, the distal section 214 of the lower foot member 210 extends distally beyond the distal end 244a of the upper foot member 240. The upper foot member 240 is coupled to the lower foot member 210 and heel member 220 proximate to the distal end 244a of the upper foot member 240 via the fasteners 230. The upper 240 and lower 210 foot members are also coupled at their proximal ends 242a, 212a. For example, in some embodiments, the proximal ends 242a, 212a of the upper 240 and lower 210 foot members are coupled to an adapter or ankle module, for example an adapter as described further below.

In some embodiments, the distal section 214 of the lower foot member 210 includes a change in curvature so that the distal section 214 has a short segment 215 of downward curvature and a toe section 219 that is downwardly vertically offset from the remainder of the lower foot member 210 proximal to the toe section 219, such as by the distance d shown in FIG. 1B. The change in curvature of the lower foot member 210 is distal to the one or more fasteners 230 coupling the heel member 220, upper foot member 240, and lower foot member 210. The change in curvature and offset toe portion 219 of the lower foot member 210 are similar to that of foot member 10 of prosthetic foot 100 as shown in FIGS. 1A-1B and described herein and provide similar benefits. In some embodiments, a crepe portion 250 can be attached to a bottom surface of a portion of the distal section 214 of the lower foot member 210. The crepe portion 250 can be similar to the crepe portion 50 of prosthetic foot 100 shown in FIGS. 1A-1B and described herein.

In some embodiments, when the prosthetic foot 200 is at rest, the upper 240 and lower 210 foot members can be separated by a gap 236 that extends between the coupled proximal ends 212a, 242a of the upper 240 and lower 210 foot members and the one or more fasteners 230. The upper 240 and lower 210 foot members can be coupled via the fasteners 230 so that there is no gap between the upper 240 and lower 210 foot members proximate the fasteners 230. A width of the gap 236 is greatest between the curved sections 246 and 216 of the upper 240 and lower 210 foot members. The width of the gap 236 gradually decreases as the prosthetic foot 200 transitions from heel-strike to toe-off during ambulation. The gradual closing of the gap during loading creates a progressive spring rate of the foot 200. As the upper 240 and lower 210 foot members come closer together, the stiffness of the prosthetic foot 200 increases, advantageously allowing for greater energy storage during mid-stance and gradual stiffening of the foot 200 relative to the load amount placed on the foot 200. The stored energy is then released during toe-off to help propel the user forward. The dual foot member deisgn also advantageously increases the strength of the prosthetic foot 200, as well as provides increased vertical displacement and enhanced suspension, as discussed above.

In some embodiments, a spacer 238 is disposed between a portion of the distal section 244 of the upper foot member 240 and the lower foot member at the location of the fasteners 230 so the lower 210 and upper 240 foot members are spaced apart near the distal end 244a of the upper foot member 240. In some embodiments, the spacer 238 allows for the gap 236 between the upper 240 and lower 210 foot members. However, the spacer 238 can be placed immediately adjacent both the upper 240 and lower 210 foot members so that there is no gap between the upper 240 and lower 210 foot members as discussed above. The spacer 238 also advantageously provides noise reduction during operation of the foot 200, for example, to reduce noise due to friction between the upper 240 and lower 210 foot members when the members 210, 240 contact each other. The spacer 238 also facilitates cleaning of the prosthetic foot 200 (e.g., cleaning the space between the upper 240 and lower 210 foot members.

The lower foot 210 and heel 220 members can define a slot 232 therebetween in the fore-aft direction at a rear portion of the prosthetic foot 100. In some embodiments, the slot 32 can taper toward a front end of the prosthetic foot 200. A resilient member 234 can be disposed between the heel member 220 and the lower foot member 210 within the slot 232. In some embodiments, the resilient member 234 can separate at least a portion of the lower foot member 210 from the heel member 220. In some embodiments, the resilient member 234 can completely separate the lower foot member 210 from the heel member 220. The resilient member 234 can be similar to resilient member 34 as shown in FIGS. 1A-1B and described herein.

In some embodiments, the upper foot member 240, lower foot member 210, and/or heel member 220 can have multiple elongate segments that can flex independently relative to each other. For example, in the illustrated embodiment, the lower foot member 210 has two elongate segments 217a, 217b that are separated from each other by a split (or slot) 218 that extends along a length between the distal end 214a and the proximal end 212a of the lower foot member 210. In some embodiments, the split 218 extends along the entire length of the lower foot member 210. In some embodiments, the split 218 extends along a length that is shorter than the entire length of the lower foot member 210. In the illustrated embodiment, the split extends from an opening in the curved portion 216 of the lower foot member 210 to the distal end 214a of the lower foot member 210. In some embodiments, the split 218 extends linearly along its length, so that the transverse width of the elongate segments 217a, 217b is generally the same along their lengths. In some embodiments, the split 218 can have a curved section, such that one of the elongate segments 217a, 217b has a different transverse width than another of the elongate segments 217a, 217b over at least a portion of their lengths.

Similarly, in the illustrated embodiment, the upper foot member 240 has two elongate segments 247a, 247b separated by a split (or slot) 248 that extends along a length between the distal end 244a and the proximal end 242a of the upper foot member 240. In some embodiments, the split 248 extends along the entire length of the upper foot member 240. In some embodiments, the split 248 extends along a length that is shorter than the entire length of the upper foot member 240. In the illustrated embodiment, the split 248 extends from an opening in the curved portion 246 of the upper foot member 240 to the distal end 244a of the upper foot member 240. In some embodiments, the split 248 extends linearly along its length, so that the transverse width of the elongate segments 247a, 247b is generally the same along their lengths. In some embodiments, the split 248 can have a curved section, such that one of the elongate segments 247a, 247b has a different transverse width than another of the elongate segments 247a, 247b over at least a portion of their lengths.

The heel member 220 can also have multiple elongate segments that can flex independently relative to each other. In the illustrated embodiment, the heel member 220 has two elongate segments 227a, 227b that are separated from each other by a split (or slot) 226 that extends along a length between the distal end 224 and the proximal end 222 of the heel member 220. In some embodiments, for example as shown in FIG. 2, the split 226 extends along the entire length of the heel member 220. In some embodiments, the split 226 extends along a length that is shorter than the entire length of the heel member 220. In some embodiments, the split 226 extends linearly along its length, so that the transverse width of the elongate segments 227a, 227b is generally the same along their lengths. In some embodiments, the split 226 can have a curved section, such that one of the elongate segments 227a, 227b has a different transverse width than another of the elongate segments 227a, 227b over at least a portion of their lengths. In some embodiments, optional splits 218, 248, and/or 226 in the lower foot member 210, upper foot member 240, and/or heel member 220 align with one another.

In some embodiments, the upper foot 240, lower foot 210, and/or heel 220 members are plate-like members with generally planar top and bottom surfaces and generally rectangular transverse cross-sections. The upper foot 240, lower foot 210, and/or heel 220 members can be made of lightweight resilient materials, such as one or more of graphite, fiberglass, carbon fiber, and the like. In some embodiments, the upper foot 240, lower foot 210, and/or heel 220 members can be formed of multiple layers of material that define a monolithic piece.

FIGS. 3A-3B illustrate an example embodiment of an adapter 300 for a prosthetic foot. The adapter 300 includes a cavity sized and shaped to receive an attachment portion near the proximal end of a prosthetic foot member, such as the proximal end 12a of foot member 10 or the proximal ends 212a, 242a of lower and upper foot members 210, 240 shown in FIGS. 1A-1B and 2A-2B, respectively, and described herein. In the illustrated embodiment, the adapter 300 includes a generally horizontal, rearwardly-facing cavity 302. In other embodiments, the cavity 302 can face, for example, downward or forward. The cavity 302 is also shaped to receive a curable material to secure the attachment portion of the prosthetic foot to the interior of the cavity 302 of the adapter 300. The adapter 300 can include one or more inlet holes 304 that are in fluid communication with the cavity 302 so that the inlet holes 304 serve as injection points for the introduction of the curable material to the cavity 302. In the illustrated embodiment, the one or more inlet holes 304 are formed in the front of the adapter 300. In other embodiments, the one or more inlet holes 304 can be formed in other surfaces of the adapter 300 (e.g., the top, a side, etc.). The curable material can be, for example, a thermosetting plastic, such as epoxy. Various types of epoxy fillings can be used, including low sag epoxy filling; however, other adhesives can be used. Anchors or barbs can be used to hold the components in place to allow for the use of other thermoplastic materials. In some embodiments, the adapter 300 can include one or more grooves (not shown) in the cavity 302 that can facilitate distribution of the adhesive about the attachment portion of the foot member. The adapter 300 can also include a connector, for example a male pyramid connector 306, for coupling the prosthetic foot to another prosthetic component, for example a pylon or socket. In some embodiments, the adapter 300 is monolithic and made of metal. Other materials are also possible.

Because the prosthetic foot is secured to the adapter 300 via the curable material rather than fasteners such as bolts, adapter 300 advantageously does not require holes to be drilled into the attachment portion of the prosthetic foot. As drilling such holes may weaken the prosthetic foot, the use of the adapter 300 and curable material helps preserve the strength of the prosthetic foot for more long-term use. Additionally, bolts and washers conventionally used to secure adapters to prosthetic feet are often made of stainless materials and can be quite heavy. The use of a lighter-weight curable material rather than bolts and washers allows for an overall reduction in weight and greater comfort for the user. Further, epoxy fillings have desirable fatigue properties and reduce the pre-stressing of the prosthetic foot when a torque is applied as compared to bolts.

Figure 4A:
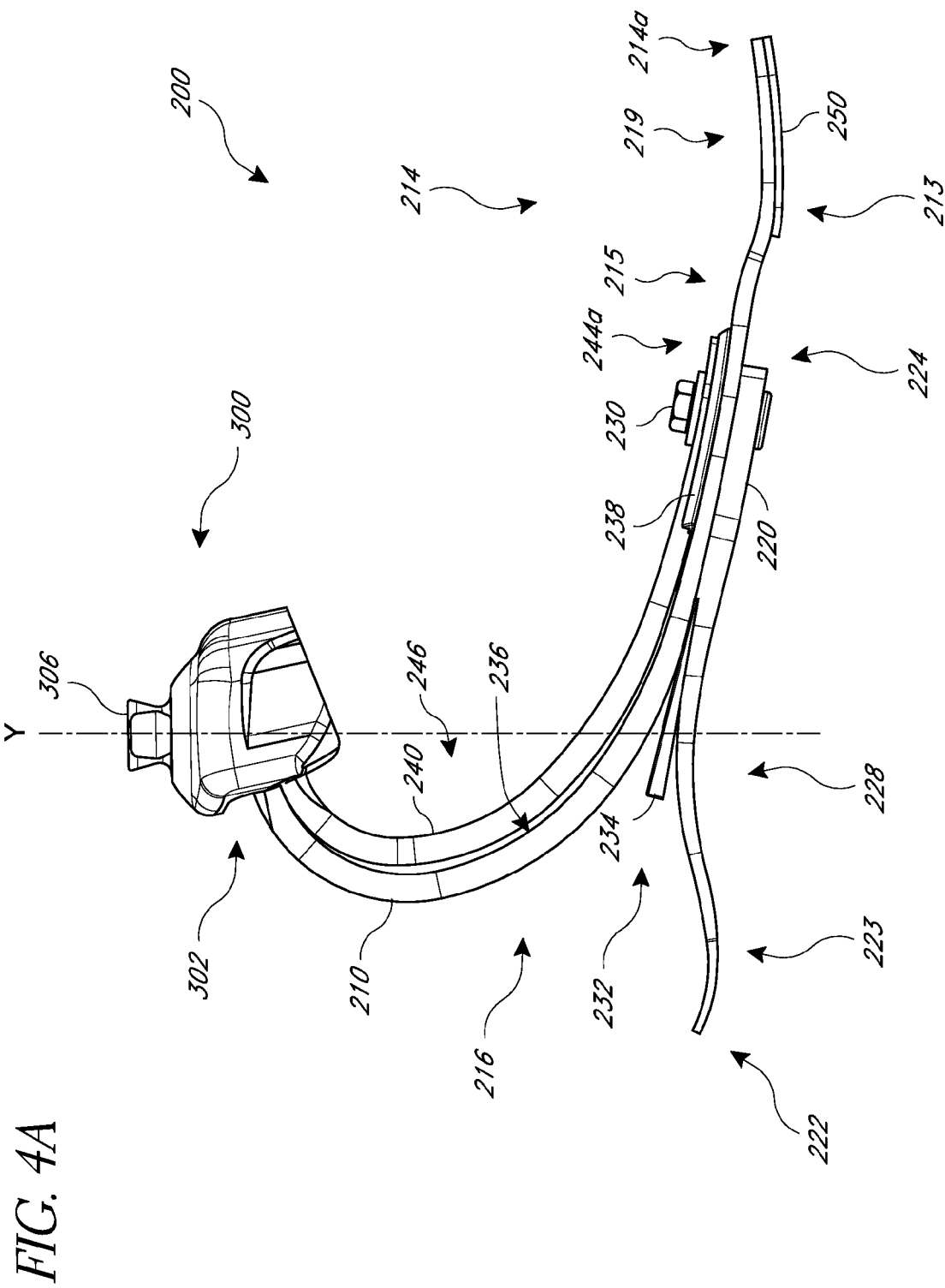
FIG. 4A is a side view of the adapter of FIGS. 3A and 3B coupled to the prosthetic foot of FIGS. 2A and 2B.
Figure 4B:
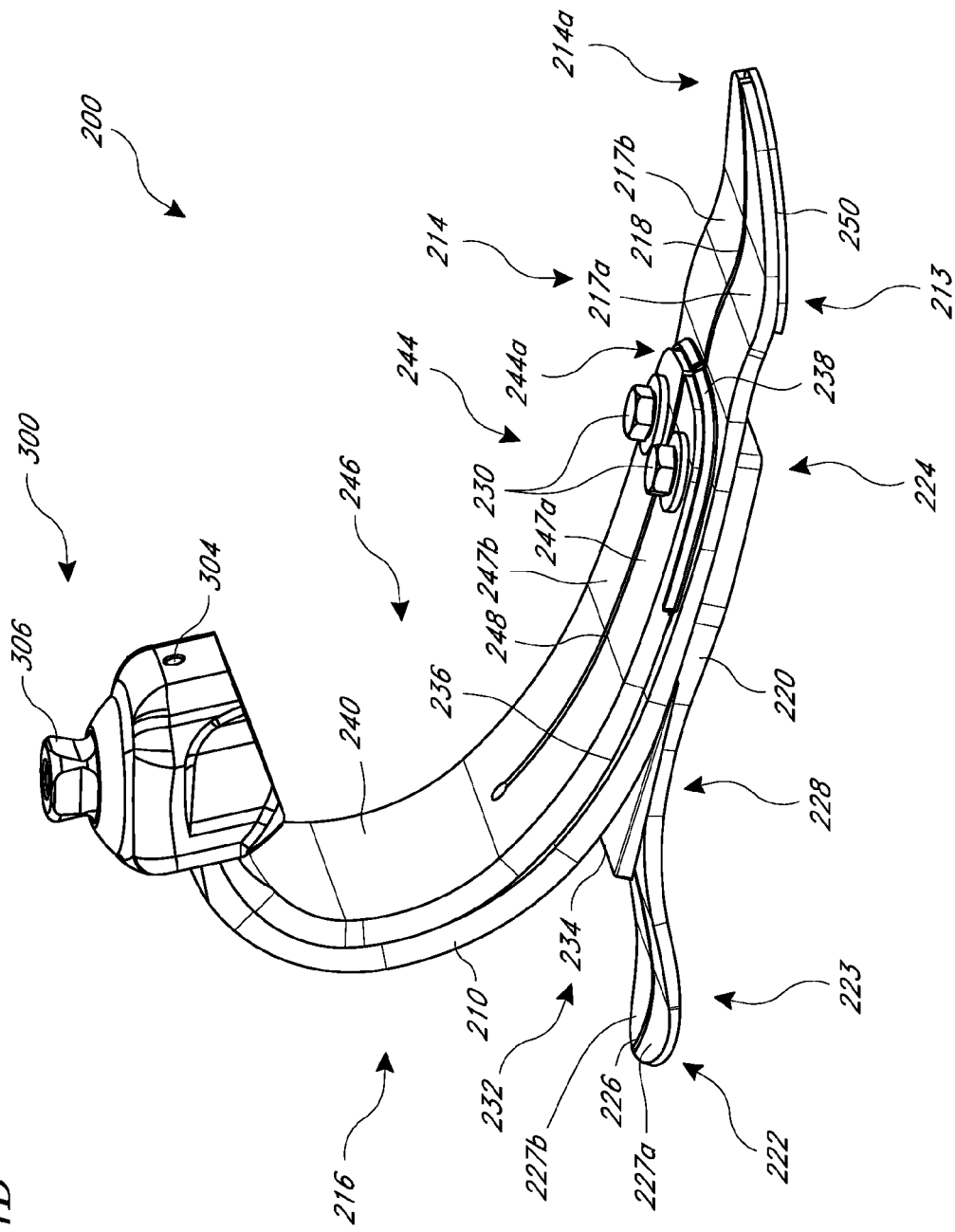
FIG. 4B is a front perspective view of the prosthetic foot of FIG. 4A.
Figure 4C:
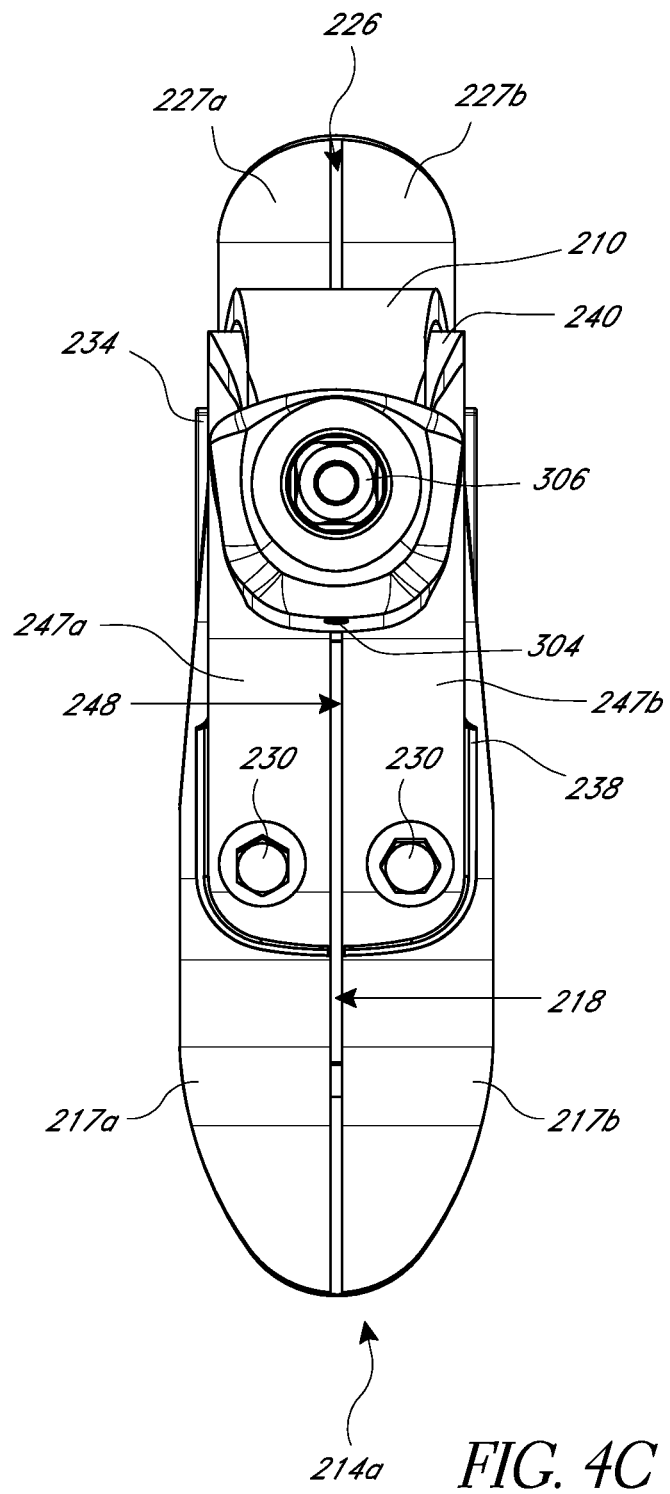
FIG. 4C is a top view of the prosthetic foot of FIG. 4A.
Figure 4E:
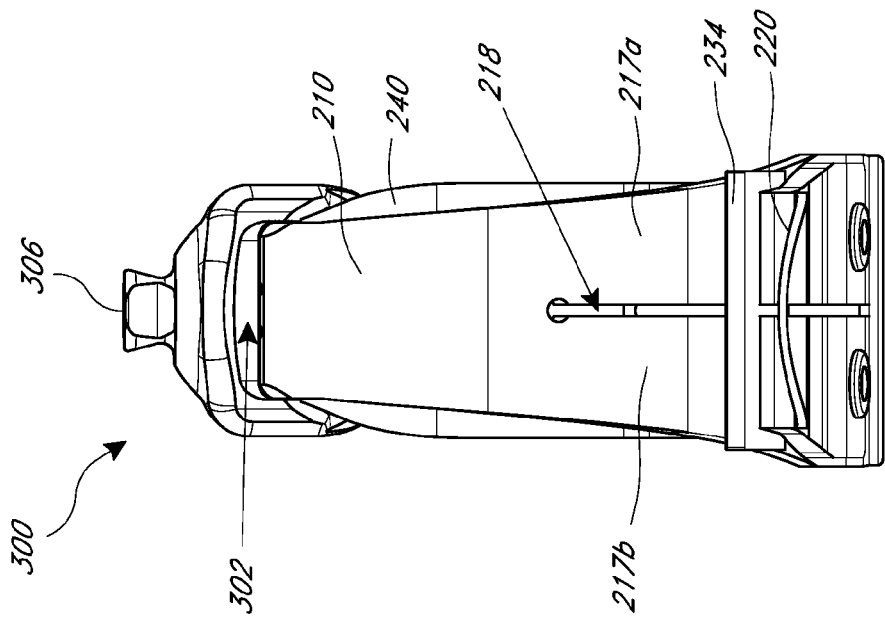
FIG. 4E is a rear view of the prosthetic foot of FIG. 4A.
Figure 4D:
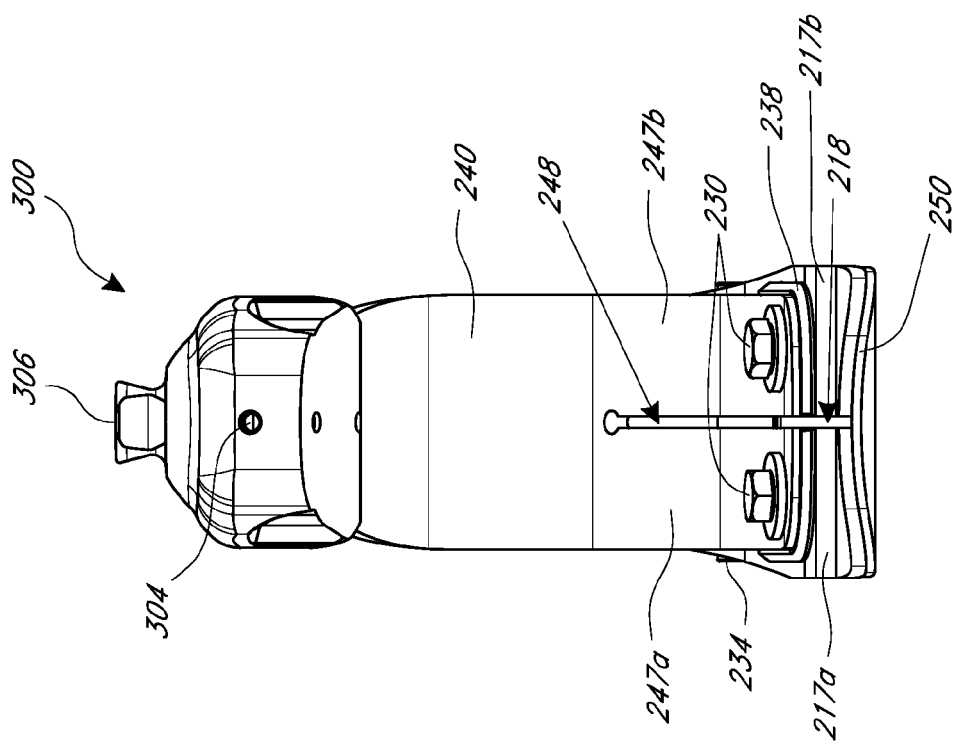
FIG. 4D is a front view of the prosthetic foot of FIG. 4A.

FIGS. 4A-4E illustrate prosthetic foot 200 coupled to the adapter 300. As shown, the rearwardly-facing cavity 302 is sized and shaped to receive portions of the proximal sections 242, 212 of the upper 240 and lower 210 foot members, and the proximal ends 242a, 212a of the upper 240 and lower 210 foot members are coupled to each other because they are coupled, e.g., glued, to the adapter 300. Pyramid connector 306 can extend along an axis Y as shown in FIG. 4A so that the curved sections 246, 216 of the upper 240 and lower 210 foot members are disposed rearward of the axis Y. The axis Y can be located at a position about one-third of the total foot 200 length measured from the proximal end 222 of the heel member 200.

In some embodiments, the prosthetic foot 100, 200 can be coupled to an insole member. The insole member can be an independent component or integrated with a foot cover or cosmesis sized to removably receive the prosthetic foot 100, 200. The insole member can have a convex upper surface that corresponds to the curvature of the concave lower surface of the arch portion 28, 228 of the prosthetic foot 100, 200 so that the heel member 20, 220 maintains contact with the insole member during ambulation from heel-strike to toe-off. The insole member can be fixedly attached to the prosthetic foot 100, 200 (e.g., via an adhesive) or removably attached. The insole member can include a resilient material such as, for example, open cell foam, closed cell foam, urethane, silicone rubber, or any other elastomer. The insole member stores and releases energy during ambulation to help fluidly guide the roll-over of the foot. In some embodiments, when the prosthetic foot 100, 200 is coupled to a cosmesis, generally only the adapter 300 extends outside the cosmesis. Example insoles and foot covers, among other things, are described in U.S. Publication No. 2010/0004757, filed Mar. 24, 2009, titled "Smooth Rollover Insole for Prosthetic Foot" and U.S. Publication No. 2006/0015192, filed May 26, 2005, titled "Functional Foot Cover," respectively, the disclosures of which are both hereby incorporated by reference in their entirety and should be considered a part of this specification.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above.

What is claimed is:

1. A prosthetic foot comprising:
a monolithic elongate foot member extending from a generally horizontal proximal portion to a generally horizontal distal portion and having a curved portion therebetween, the proximal portion of the foot member configured to be coupled to an adapter, wherein the distal portion comprises a change in curvature that defines a toe region of the foot member such that a top surface of the toe region is downwardly vertically offset from a top surface of a portion of the foot member proximal of the change in curvature, wherein the change in curvature is discontinuous, and wherein the foot member has a forwardly-facing concave portion extending from the proximal portion to the change in curvature.

2. The prosthetic foot of claim 1, wherein a radius of curvature of the toe region as viewed from a side of the foot is the same as a radius of curvature of the portion of the foot member proximal to the change in curvature as viewed from the side of the foot.

3. The prosthetic foot of claim 2, wherein the change in curvature occurs in top and bottom surfaces of the foot member.

4. The prosthetic foot of claim 1, wherein the toe region and the portion of the foot member proximal to the change in curvature are concave and the change in curvature comprises a forwardly facing convex segment.

5. The prosthetic foot of claim 1, wherein the toe region is vertically offset from the portion of the foot member proximal to the change in curvature by a distance of about 0 to about 15 mm.

6. The prosthetic foot of claim 1, wherein the change in curvature is at a location corresponding to a metatarsal region of a natural human foot.

7. The prosthetic foot of claim 1, further comprising an elongated heel member extending rearwardly from a distal end to a free proximal end, wherein the heel member is coupled to the elongate foot member proximate the distal end of the heel member and proximal to the change in curvature in the elongate foot member.

8. The prosthetic foot of claim 1, wherein the change in curvature in the elongate foot member is configured to facilitate support of a user's weight during stance by the prosthetic foot near the proximal end of the heel member and the toe region of the foot member.

9. The prosthetic foot of claim 1, further comprising an attachment adapter comprising a cavity configured to at least partially receive the proximal end of the foot member therein.

10. The prosthetic foot of claim 9, wherein the foot member is secured to the adapter via an adhesive.

11. A prosthetic foot comprising:
an elongate upper foot member extending from a proximal end to a distal end, the proximal end configured to be coupled to an adapter, the upper foot member comprising a concave portion between the proximal and distal ends of the upper foot member; and
an elongate lower foot member extending from a proximal end to a distal end, the proximal end configured to be coupled to the adapter, wherein the lower foot member is positioned below the upper foot member and the lower foot member extends distally beyond the distal end of the upper foot member to form a toe region, the lower foot member comprising a concave portion between the proximal and distal end of the lower foot member;
wherein the proximal end of the upper foot member is coupled to the proximal end of the lower foot member and the upper and lower foot members are coupled by one or more fasteners proximate the distal end of the upper foot member;
wherein the lower foot member comprises a change in curvature distal to the one or more fasteners so that a top surface of the toe region is downwardly vertically offset from a top surface of a portion of the lower foot member proximal of the change in curvature, wherein the change in curvature comprises a forwardly-facing convex segment and occurs in top and bottom surfaces of the lower foot member; and
wherein the upper and lower foot members are separated by a gap when the prosthetic foot is at rest, the gap extending between the coupled proximal ends of the upper and lower foot members and the one or more fasteners, wherein the gap narrows during ambulation.

12. The prosthetic foot of claim 11, wherein the upper foot member includes a split that separates the upper foot member into a medial blade and a lateral blade, wherein the split extends from an opening in the concave portion to the distal end of the upper foot member.

13. The prosthetic foot of claim 11, wherein the lower foot member includes a split that separates the lower foot member into a medial blade and a lateral blade, wherein the split extends from an opening in the concave portion to the distal end of the lower foot member.

14. The prosthetic foot of claim 11, further comprising an attachment adapter comprising a cavity configured to at least partially receive the proximal ends of the upper and lower foot members therein.

15. The prosthetic foot of claim 14, wherein the upper and lower foot members are secured to the adapter via an adhesive.

16. The prosthetic foot of claim 11, further comprising a spacer disposed between the distal end of the upper foot member and the lower foot member, wherein the spacer at least partially defines the gap separating the upper and lower foot members.

17. The prosthetic foot of claim 11, further comprising an elongated heel member extending from a free proximal end to a distal end, wherein the heel member is coupled to the lower foot member via the at least one fastener proximate the distal end of the heel member.

18. The prosthetic foot of claim 11, wherein the lower foot member is monolithic.

19. The prosthetic foot of claim 11, wherein the lower foot member comprises a constant thickness from the proximal end to the distal end.

20. A prosthetic foot comprising:
an elongate upper foot member extending from a proximal end to a distal end, the proximal end configured to be coupled to an adapter; and
a monolithic elongate lower foot member extending from a proximal end to a distal end, wherein the lower foot member is positioned below the upper foot member and the lower foot member extends distally beyond the distal end of the upper foot member to define a toe region;
wherein the upper and lower foot members are coupled proximate the distal end of the upper foot member;
wherein a distal portion of the lower foot member curves downward via a convex segment to the toe region of the lower foot member so that the toe region is downwardly vertically offset from a portion of the lower foot member proximal of the convex segment, wherein said convex segment at least partially defines a change in a radius of curvature of said distal portion of the lower foot member that is discontinuous.

21. The prosthetic foot of claim 20, wherein a radius of curvature of the toe region as viewed from a side of the foot is the same as a radius of curvature of the portion of the foot member proximal to the convex segment as viewed from the side of the foot.

* * * * *

UNITED STATES PATENT AND TRADEMARK OFFICE
CERTIFICATE OF CORRECTION

| | | |
|---|---|---|
| PATENT NO. | : 9,017,421 B2 | Page 1 of 1 |
| APPLICATION NO. | : 13/309418 | |
| DATED | : April 28, 2015 | |
| INVENTOR(S) | : Christophe Lecomte et al. | |

It is certified that error appears in the above-identified patent and that said Letters Patent is hereby corrected as shown below:

In the Claims

In column 12, line 45, in claim 20, change "re ion" to --region--.

Signed and Sealed this
Tenth Day of May, 2016

Michelle K. Lee
*Director of the United States Patent and Trademark Office*